(12) United States Patent
Yamagishi

(10) Patent No.: US 7,833,763 B2
(45) Date of Patent: Nov. 16, 2010

(54) METHOD FOR PRODUCING ORGANIC ACID

(75) Inventor: Kenji Yamagishi, Zushi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 425 days.

(21) Appl. No.: 11/319,471

(22) Filed: Dec. 29, 2005

(65) Prior Publication Data

US 2006/0172401 A1 Aug. 3, 2006

Related U.S. Application Data

(63) Continuation of application No. PCT/JP2004/010080, filed on Jul. 8, 2004.

(30) Foreign Application Priority Data

Jul. 9, 2003 (JP) ............................. 2003-194240

(51) Int. Cl.
C12P 7/54 (2006.01)
C12P 7/46 (2006.01)

(52) U.S. Cl. ................... 435/145; 435/140; 435/252.3; 435/252.31; 435/252.33; 435/252.7

(58) Field of Classification Search ....................... None
See application file for complete search history.

(56) References Cited

U.S. PATENT DOCUMENTS

| | | |
|---|---|---|
| 4,489,160 A | 12/1984 | Katsumata et al. |
| 4,500,640 A | 2/1985 | Katsumata et al. |
| 4,514,502 A | 4/1985 | Miwa et al. |
| 4,617,267 A | 10/1986 | Katsumata et al. |
| 5,034,105 A | 7/1991 | Berglund et al. |
| 5,132,456 A | 7/1992 | King et al. |
| 5,142,834 A | 9/1992 | Laclave et al. |
| 5,143,833 A | 9/1992 | Datta |
| 5,143,834 A | 9/1992 | Glassner et al. |
| 5,168,055 A | 12/1992 | Datta et al. |
| 5,185,262 A | 2/1993 | Kohama et al. |
| 5,504,004 A | 4/1996 | Guettler et al. |
| 5,770,435 A | 6/1998 | Donnelly et al. |
| 5,827,700 A | 10/1998 | Felman et al. |
| 5,869,301 A | 2/1999 | Nghiem et al. |
| 5,958,744 A | 9/1999 | Berglund et al. |
| 5,977,331 A | 11/1999 | Asakura et al. |
| 6,008,384 A * | 12/1999 | Bockrath et al. ............. 549/508 |
| 6,265,190 B1 | 7/2001 | Yedur et al. |
| RE37,393 E * | 9/2001 | Donnelly et al. ........ 435/252.33 |
| 6,448,061 B1 | 9/2002 | Pan et al. |
| 6,455,284 B1 | 9/2002 | Gokarn et al. |
| 6,656,701 B2 * | 12/2003 | Bishop et al. ................. 435/23 |
| 6,696,561 B1 | 2/2004 | Pompejus et al. |
| 2002/0055152 A1 | 5/2002 | Farwick et al. |
| 2002/0150999 A1 | 10/2002 | Dusch et al. |
| 2002/0197605 A1 | 12/2002 | Nakagawa et al. |
| 2003/0017559 A1 | 1/2003 | Donnelly et al. |
| 2003/0069354 A1 | 4/2003 | Oyasato et al. |
| 2003/0087381 A1 | 5/2003 | Gokarn et al. |
| 2003/0100079 A1 | 5/2003 | Mockel et al. |
| 2005/0196848 A1 | 9/2005 | Dusch et al. |
| 2006/0046288 A1 | 3/2006 | Ka-Yiu et al. |
| 2006/0205048 A1 | 9/2006 | Murase et al. |
| 2006/0228712 A1 | 10/2006 | Nakagawa et al. |
| 2006/0276674 A1 | 12/2006 | Kushiku et al. |
| 2006/0281156 A1 | 12/2006 | Aoyama et al. |
| 2007/0087423 A1 | 4/2007 | Murakami et al. |
| 2007/0154999 A1 | 7/2007 | Fukui et al. |
| 2009/0156779 A1 | 6/2009 | Murase et al. |

FOREIGN PATENT DOCUMENTS

| | | |
|---|---|---|
| CA | 2 322 553 | 4/2001 |
| EP | 0075612 | 4/1983 |
| EP | 0078537 | 5/1983 |
| EP | 0 389 103 | 9/1990 |
| EP | 0410728 | 1/1991 |
| EP | 1 096 013 | 5/2001 |
| EP | 1 108 790 | 6/2001 |
| EP | 1 748 062 | 1/2007 |
| JP | 57-134500 | 8/1982 |
| JP | 57-183799 | 11/1982 |
| JP | 58-035197 | 3/1983 |
| JP | 58-067679 | 4/1983 |
| JP | 58-077895 | 5/1983 |
| JP | 58-192900 | 11/1983 |
| JP | 61-209596 | 9/1986 |
| JP | 62-048394 | 3/1987 |
| JP | 62-238231 | 10/1987 |
| JP | 62-238232 | 10/1987 |
| JP | 62-294090 | 12/1987 |
| JP | 1-191686 | 8/1989 |

(Continued)

OTHER PUBLICATIONS

Guettler et al. "*Actinobacillus succinogenes* sp. Nov., a novel succinic-acid-producing strain from the bovine rumen", International Journal of Systematic Bacteriology (1999), vol. 49, pp. 207-216, cited in the specification, beginning on p. 1, lines 10-11.

(Continued)

*Primary Examiner*—Herbert J. Lilling
(74) *Attorney, Agent, or Firm*—Greenblum & Bernstein, P.L.C.

(57) ABSTRACT

An object to be solved by the present invention is to provide a method for producing organic acid with higher fermentation efficiency. The present invention provides a method for producing organic acid from an organic material by allowing bacterial cell or treated products thereof to act on an aqueous reaction solution containing the above organic material, which is characterized in that after completion of the reaction, the aqueous reaction solution is recovered, cell or treated products thereof are separated from the recovered aqueous reaction solution, and the separated cell or treated products thereof are allowed to act on a fresh aqueous reaction solution, so that the cell or treated products thereof are repeatedly used.

13 Claims, No Drawings

FOREIGN PATENT DOCUMENTS

| | | |
|---|---|---|
| JP | 2-072876 | 3/1990 |
| JP | 2-283289 | 11/1990 |
| JP | 3-072891 | 3/1991 |
| JP | 3-151884 | 6/1991 |
| JP | 3-210184 | 9/1991 |
| JP | 5-260985 | 10/1993 |
| JP | 6-14781 | 1/1994 |
| JP | 7-67683 | 3/1995 |
| JP | 7-304839 | 11/1995 |
| JP | 11-113588 | 4/1999 |
| JP | 11-130852 | 5/1999 |
| JP | 11-196887 | 7/1999 |
| JP | 11-196888 | 7/1999 |
| JP | 11-206385 | 8/1999 |
| JP | 2000-500333 | 1/2000 |
| JP | 2000-037196 | 2/2000 |
| JP | 2001-161386 | 6/2001 |
| JP | 2001-190297 | 7/2001 |
| JP | 2001-514900 | 9/2001 |
| JP | 2002-511250 | 4/2002 |
| JP | 2002-191370 | 7/2002 |
| JP | 2002-291477 | 10/2002 |
| JP | 2003-171448 | 6/2003 |
| JP | 2003-199522 | 7/2003 |
| JP | 2003-235592 | 8/2003 |
| JP | 2003-235593 | 8/2003 |
| JP | 2005-095169 | 4/2005 |
| JP | 2006-238843 | 9/2006 |
| JP | 2006-320208 | 11/2006 |
| WO | 95/34672 | 12/1995 |
| WO | 97/16528 | 5/1997 |
| WO | 99/06532 | 2/1999 |
| WO | 99/09190 | 2/1999 |
| WO | 99/53035 | 10/1999 |
| WO | 01/66508 | 9/2001 |
| WO | 02/29020 | 4/2002 |
| WO | 02/36797 | 5/2002 |
| WO | 02/072855 | 9/2002 |
| WO | 03/040290 | 5/2003 |
| WO | 2005/005649 | 1/2005 |
| WO | 2005/010182 | 2/2005 |
| WO | 2005/021770 | 3/2005 |
| WO | 2005/026349 | 3/2005 |
| WO | 2005/030973 | 4/2005 |
| WO | 2005/113744 | 12/2005 |
| WO | 2005/113745 | 12/2005 |
| WO | 2006/020663 | 2/2006 |
| WO | 2006/031424 | 3/2006 |
| WO | 2006/034156 | 3/2006 |
| WO | 2006/069174 | 6/2006 |
| WO | 2007/046389 | 4/2007 |
| WO | 2007/099867 | 9/2007 |

OTHER PUBLICATIONS

C.S. Gong, et al., "Production of L-Malic Acid from Fumaric Acid by Resting Cells of *Brevibacterium sp.*," Applied Biochemistry and Biotechnology (1996), vol. 57/58, pp. 481-487.
Akihiko Mori, "Su no Hanashi 51 Sakusankin no Hakko Seiri (15)", Shokuhin to Kagaku (2002), vol. 44, No. 4, pp. 43-49.
English Language Abstract of JP 11-113588.
English Language Abstract of JP 5-260985.
English Language Abstract of JP 62-048394.
English Language Abstract of JP 61-209596.
English Language Abstract of JP 11-206385.
English Language Abstract of JP 7-304839.
English Language Abstract of JP 11-130852.
English Language Abstract of JP 2003-171448.
English Language Abstract of JP 2003-235593.
U.S. Appl. No. 11/561,011, filed Nov. 17, 2006, Fukui et al.
U.S. Appl. No. 12/104,595, filed Apr. 17, 2008, Koseki et al.
U.S. Appl. No. 12/090,431, filed Apr. 16, 2008, Koseki et al.
English Language Abstract of JP 3-072891.
English Language Abstract of JP 6-014781.
English Language Abstract of JP 7-67683.
English Language Abstract and computer translation of JP 11-196887.
English Language Abstract of JP 11-196888.
English Language Abstract of JP 62-238231.
English Language Abstract of JP 62-238232.
English Language Abstract of JP 2000-037196.
English Language Abstract of JP 2001-161386.
English Language Abstract of JP 2001-190297.
English Language Abstract of JP 2002-191370.
English Language Abstract and computer translation of JP 2002-291447.
English Language Abstract of JP 2003-199522.
English Language Abstract of JP 2003-235592.
BA et al. *Biomacromolecules* 4: 1827-1834, 2003.
Bott et al. *Journal of Biotechnology* 104:129-153, 2003.
Branden et al. *Introduction to Protein Structure*, Garland Publishing Inc., New York, p. 247, 1991.
Calvary et al. *Microchemical Journal* 23(4):473-480, 1978.
Chotani et al. *Biochimica et Biophysica Acta, Protein Structure and Molecular Enzymology* 1543(2):434-455, 2000.
Database UniProt, Accession No. Q8NMK4, Oct. 1, 2002.
Database EPO Proteins, Accession No. AX771820, Jul. 2, 2003.
Database EMBL, Accession No. AX771819, Jul. 2, 2003.
Database Geneseq, Accession No. AAG92572, Sep. 26, 2001.
Database EMBL, Accession No. AX122910, May 10, 2001.
Database UniProt, Accession No. Q6M2R3, Jul. 5, 2004.
Gokarn et al. *Biotechnology Letters* 20(8): 795-798, 1998.
Gokarn et al. *Applied and Environmental Microbiology* 66(5):1844-1850, 2000.
Gokarn et al. *Appl. Microbial. Biotechnol.* 56:188-195, 2001.
Goldberg et al. *Applied and Environmental Microbiology* 45(6): 1838-1847, 1983.
Hong et al. *Biotechnology and Bioengineering* 74(2):89-95, 2001.
Hong et al. *Applied Microbiology and Biotechnology* 58:286-290, 2002.
Inui et al. *J. of Mol. Microbiol. and Biotech.* 7(4):182-196, 2004.
Kalinowski et al. *J. of Biotech.* 104(1-3):5-25, 2003.
Kegg Database on-line, NCg10359, 2006.
Kegg Database on-line, NCg10360, 2006.
Kegg Database on-line, NCg10361, 2006.
Kirchner et al. *J. of Biotech.* 104(1-3):287-299, 2003.
Kurokawa et al. *Arch. Microbiol.* 183:317-324, 2005.
Lin et al. *Applied Genetics and Molecular Biotechnology*, published online: Nov. 24, 2004, total pp. 16.
Mat-Jan et al. *Journal of Bacteriology* 171(1):342-348, 1989.
Maxa et al. *Mitteilungen Klosterneuburg* 41(6):233-237, 1991.
Millard et al. *Applied and Environmental Microbiology* 62(5):1808-1810, 1996.
Reinscheid et al. *Microbiology* 145:503-513, 1999.
Schnorpfeil et al. *Eur. J. Biochem.* 268:3069-3074, 2001.
Seffernick et al. *J. Bacteriol.* 183(8): 2405-2410, 2001.
Stols et al. *Applied and Environmental Microbiology* 63(7):2695-2701, 1997.
Wang et al. *Applied Biochemistry and Biotechnology* 70-72:919-928, 1998.
Witkowski et al. *Biochemistry* 38:11643-11650, 1999.
Zeikus et al. *Appl. Microbiol. Biotechnol.* 51:545-552, 1999.
English Language Abstract of JP 1-191686, Aug. 1, 1989.
English Language Abstract of JP 2-072876, Mar. 13, 1990.
English Language Abstract of JP 3-210184, Sep. 13, 1991.
English Language Abstract of JP 57-134500, Aug. 19, 1982.
English Language Abstract of JP 57-183799, Nov. 12, 1982.
English Language Abstract of JP 58-035197, Mar. 1, 1981.
English Language Abstract of JP 58-077895, May 11, 1983.
English Language Abstract of JP 58-192900, May 11, 1983.
English Language Abstract of JP 2005-095169, Apr. 14, 2005.
English Language Abstract of JP 2006-238843, Sep. 14, 2006.
English Language Abstract of JP 2006-320208, Nov. 30, 2006.
Arikawa et al. *J. Biosci. Bioeng.* 87(1):28-36, 1999.

Chang et al. *J. Bacteriol.* 151:1279-1289, 1982.
Dunn et al. *J. Bacteriol.* 178:5960-5970, 1996.
Gergely et al. *J. Biol. Chem.* 198:323-334, 1952.
Imabori et al. "Seikagaku Jiten" Dai 3 Pan Tokyo Kagaku Dojin, Oct. 8, 1998, p. 392-393.
Jaurin et al. GenBank Accession No. J01611, Feb. 2000.
Kanarek et al. *J. Biol. Chem.* 239:4202-4206, 1964.
Klotzsch et al., *Meth. Enzymol.* 12:381-386, 1969.
Kondo et al. *Gene* 191:47-50, 1997.
Lehn et al. *Gene* 165:331-332, 1995.
Liebl et al. *International Journal of Systematic Bacteriology* 41:255-260, 1991.
Mackay et al. *Biochem. Biophys. Res. Comm.* 202:1009-1014, 1994.
Maklashina et al. *J. Bacteriol.* 180(22):5989-5996, 1998.
Peters-Windisch et al. *Microbiology* 144:915-927, 1998.
Ramponi, *Meth. Enzymol.* 42:409-426, 1975.
Schafer et al., *Gene* 145:69-73, 1994.
Shiio et al. *Agric. Biol. Chem.* 44(8):1897-1904, 1980.
Song et al. *Enzyme Microbiol. Technol.* 39:352-361, 2006.
Stucka et al. *Mol. Gen. Genet.* 229:307-315, 1991.
Tomar et al. *Appl. Microbiol. Biotechnol.* 62:76-82, 2003.
Torino et al. *J. Appl. Microbiol.* 91:846-852, 2001.
Uematsu et al. *Plant Cell Reports* 10:286-290, 1991.
Usuda et al. *Microbiology* 142:3347-3354, 1996.
Vertes et al. *Res. Microbiol.* 144:181-185, 1993.
Whisstock et al. *Q. Rev. Biophysics* 36(3):307-340, 2003.
Zhang et al. *Proc. Natl. Acad. Sci. USA* 90:1766-1770, 1993.
NP_ 601767, NCBI Sequence Viewer. Acetyl-CoA hydrolase, dated Dec. 14, 2006.
NP_ 601811, NCBI Sequence Viewer, Pyruvate Dehyrogenase, dated Dec. 14, 2006.

* cited by examiner

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (9)
<223> OTHER INFORMATION: n stands for any base
<220> FEATURE:
<221> NAME/KEY: misc_feature
<222> LOCATION: (12)
<223> OTHER INFORMATION: n stands for any base

<400> SEQUENCE: 1
caraarccng gngarac                                                 17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (3)
<223> OTHER INFORMATION: n stands for any base
<220> FEATURE:
<221> NAME/KEY: misc_feature
<222> LOCATION: (12)
<223> OTHER INFORMATION: n stands for any base
<220> FEATURE:
<221> NAME/KEY: misc_feature
<222> LOCATION: (15)
<223> OTHER INFORMATION: n stands for any base

<400> SEQUENCE: 2
tcnccrtgyt cnccnat                                                 17
```

METHOD FOR PRODUCING ORGANIC ACID

This is a continuation of International Application No. PCT/JP2004/010080, filed Jul. 8, 2004, the contents of which are expressly incorporated by reference herein in its entirety.

TECHNICAL FIELD

The present invention relates to a method for producing organic acid using bacteria.

BACKGROUND ART

When succinic acid or the like is produced by fermentation, anaerobic bacteria such as *Anaerobiospirillum* or *Actinobacillus* are generally used (U.S. Pat. Nos. 5,143,834 and 5,504,004, and International Journal of Systematic Bacteriology (1999), 49, 207-216). When anaerobic bacteria are used, the yield of the products is high. However, since many nutrients are required for the growth of the bacteria, it is necessary to add a large amount of organic nitrogen source such as CSL (corn steep liquor) to a medium. Such addition of a large amount of organic nitrogen source causes not only an increase in the cost of the medium, but also an increase in the cost of purification of products when the products are taken out. Thus, it is not economical.

A method is known which comprises: culturing aerobic bacteria under aerobic conditions to allow cell to grow; collecting and washing the cell; and producing organic acids from static cell without aerating oxygen (JP Patent Publication (Kokai) No. 11-113588 A (1999)). In this case, only a small amount of organic nitrogen may be added to allow cell to grow, and the cell can sufficiently grow in a simple medium. Thus, this method is economical. However, the production amount of organic acid of interest and the production rate per cell are still insufficient. Therefore, it is desired that a more excellent method is established.

In addition, another method is known which involves a continuous culture in which bacteria are repeatedly cultured to produce L-glutamic acid or L-asparatic acid (JP Patent Publication (Kokai) Nos. 62-48394 A (1987) and 5-260985 A (1993)). However, to date, there have been no reports regarding a method for producing succinic acid by repeatedly culturing bacteria such as coryneform bacteria, *Bacillus* bacteria, or *Rhizobium* bacteria, particularly under anaerobic conditions.

DISCLOSURE OF THE INVENTION

An object to be solved by the present invention is to provide a method for producing organic acid with higher fermentation efficiency.

As a result of intensive studies directed towards achieving the aforementioned object, the present inventors have found that the production rate and yield of organic acid are increased by reusing cell, which have been used in one or more production processes. The present invention has been completed based on these findings.

Thus, the present invention provides the followings:

(1) A method for producing organic acid from an organic material by allowing bacterial cell or treated products thereof to act on an aqueous reaction solution containing the above organic material, which is characterized in that after completion of the reaction, the aqueous reaction solution is recovered, cell or treated products thereof are separated from the recovered aqueous reaction solution, and the separated cell or treated products thereof are allowed to act on a fresh aqueous reaction solution, so that the cell or treated products thereof are repeatedly used.

(2) The method according to (1) above, wherein the bacteria are any one selected from the group consisting of coryneform bacteria, *Bacillus* bacteria, and *Rhizobium* bacteria.

(3) The method according to (1) or (2) above, wherein the bacteria are mutant bacteria, whose ability to produce lactic acid is reduced to 10% or less when compared with that of wild-type bacteria.

(4) The method according to any one of (1) to (3) above, wherein bacteria which lack lactate dehydrogenase (LDH) are used.

(5) The method according to any one of (1) to (4) above, wherein the reaction solution contains carbonate ion, bicarbonate ion, or carbon dioxide.

(6) The method according to any one of (1) to (5) above, wherein the bacterial cell or treated products thereof are allowed to act on the aqueous reaction solution containing the organic material under an anaerobic atmosphere.

(7) The method according to any one of (1) to (6) above, wherein the organic material is glucose.

(8) The method according to any one of (1) to (7) above, wherein the number of reuse of the cell or treated products thereof is 3 or more times.

(9) The method according to any one of (1) to (8) above, wherein the organic acid is succinic acid, malic acid, or fumaric acid.

(10) The method according to any one of (1) to (9) above, wherein after completion of the reaction, the total amount of the aqueous reaction solution is used as it is in the subsequent reaction.

(11) The method according to any one of (1) to (10) above, wherein the amount of organic acid produced in the second process and the subsequent processes is 80% or more with respect to the production amount thereof in the first process.

(12) The method according to any one of (1) to (11) above, wherein the amount of succinic acid produced in the second process and the subsequent processes is 80% or more with respect to the production amount thereof in the first process.

(13) An organic acid-containing composition which is produced by the method of any one of (1) to (12) above.

(14) The organic acid-containing composition according to (13) above, wherein the organic acid is succinic acid.

(15) A method for producing an organic acid-containing polymer, which comprises the steps of: producing organic acid by the method of any one of (1) to (12) above; and performing a polymerization reaction using the obtained organic acid as a starting material.

(16) The method for producing an organic acid-containing polymer according to (15) above, wherein the organic acid is succinic acid.

BEST MODE FOR CARRYING OUT THE INVENTION

The embodiments of the present invention will be described in detail below.

The present invention resides in a method for producing organic acid which is characterized in that 50% or more of cell used in one or more production processes are reused in the production of organic acid by a reaction using bacterial cell. When lactic acid was intended to be produced by anaerobic fermentation using coryneform bacteria, the production amount of lactic acid was significantly reduced as the cell are repeatedly used. In contrast, it was found that in the present invention, the production amount of, in particular succinic acid, is not reduced even if cell is repeatedly used.

In the method of the present invention, when organic acid is produced from an organic material by allowing bacterial cell or treated products thereof to act on an aqueous reaction solution containing the above organic material, the aqueous reaction solution is recovered after completion of the synthesis reaction of organic acid, the cell or treated products thereof are separated from the recovered aqueous reaction solution, and the separated cell or treated products thereof are allowed to act on a fresh aqueous reaction solution, so that the production of organic acid can be repeatedly carried out. As stated above, the method of the present invention is characterized in that cell or treated products thereof are repeatedly used.

Bacteria used in the present invention are not particularly limited, as long as they have an ability to produce organic acid. Among them, aerobic bacteria such as *Bacillus, Rhizobium*, or coryneform bacteria are preferable.

Among the above aerobic bacteria, coryneform bacteria are preferable. Preferred examples of such coryneform bacteria may include microorganisms belonging to *Corynebacterium*, microorganisms belonging to *Brevibacterium*, and microorganisms belonging to *Arthrobacter*. Of these, microorganisms belonging to *Corynebacterium* and *Brevibacterium* are preferable. More preferred examples may include microorganisms belonging to *Corynebacterium glutamicum, Brevibacterium flavum, Brevibacterium ammoniagenes*, and *Brevibacterium lactofermentum*.

Particularly preferred examples of the above microorganisms may include *Brevibacterium flavum* MJ-233 (FERM BP-1497), *Brevibacterium flavum* MJ-233AB-41 (FERM BP-1498), *Brevibacterium ammoniagenes* ATCC6872, *Corynebacterium glutamicum* ATCC31831, and *Brevibacterium lactofermentum* ATCC13869.

The aforementioned microorganisms used for the method of the present invention include not only wild-type strains, but also any strains of mutant strains obtained by ordinary mutagenesis such as UV irradiation or an NTG treatment or recombinant strains obtained by cell fusion or genetic means such as gene recombination. As a host for the above gene recombinant strain, either the same genus as the parent strain, or a genus different from the parent strain may be used, as long as it is a microorganism that can be transformed. Preferably, the aerobic bacteria as mentioned above are used as hosts.

Among these strains, the use of a mutant strain which lacks lactate dehydrogenase is more effective in the present reaction. The method described in JP Patent Publication (Kokai) No. 11-205385 A (1999) is an example of the method for producing a mutant strain of the coryneform bacteria, which lacks lactate dehydrogenase. A mutant strain lacking lactate dehydrogenase can easily be produced according to this method.

In the present invention, products which are obtained by treating cell can also be used. Examples of such treated products of cell may include immobilized cell obtained by immobilizing cell with acrylamide, carrageenan or the like, disintegrated products obtained by disintegrating cell, supernatants thereof obtained by centrifugation, and fractions thereof obtained by partially purifying the supernatants by an ammonium sulfate treatment or the like. In order to use aerobic coryneform bacteria for the method of the present invention, it is preferable to first culture cell under common aerobic conditions and then to use them. A medium used in the common culture of microorganisms can be used herein. For example, a common medium prepared by adding a natural nutrient such as a meat extract, yeast extract or peptone to a composition consisting of an inorganic salt such as ammonium sulfate, potassium phosphate or magnesium sulfate, can be used. Cultured cell is recovered by centrifugation, membrane separation or the like, and they are used in the following reaction.

With regard to the use of the above-described bacteria in the present reaction, those which have been subjected to a slant culture in a solid medium such as an agar medium may be directly used in the reaction. However, bacteria which have previously been subjected to a culture in a liquid medium (a seed culture) are preferably used.

An organic material of a medium used in the culture and reaction of these bacteria is not particularly limited, as long as it is a carbon source which can be assimilated by these microorganisms. Examples of such an organic material that is generally used may include fermentable sugars including: carbohydrates such as galactose, lactose, glucose, fructose, glycerol, sucrose, saccharose, starch, or cellulose; and polyalcohols such as glycerin, mannitol, xylitol, or ribitol. Of these, glucose, fructose and glycerol are preferable, and glucose is particularly preferable.

Also, a starch-saccharified solution or molasses which contain the above-described fermentable sugars, may be used. These fermentable sugars can be used either alone or in combination.

The concentration of the above carbon source used is not particularly limited. It is advantageous to increase the concentration as high as possible to the extent that it does not inhibit the generation of organic acid. The reaction is carried out within the range generally between 5% and 30% (W/V), and preferably between 10% and 20% (W/V).

Moreover, a supplementary carbon source may be added depending on a reduction of the above carbon source, which occurs due to the progression of the reaction.

A nitrogen source is not particularly limited, as long as it can be assimilated by the microorganisms. Specific examples of such a nitrogen source may include various types of organic and inorganic nitrogen compounds such as an ammonium salt, nitrate, urea, soybean hydrolysate, casein lysate, peptone, yeast extract, meat extract, or corn steep liquor.

Examples of an inorganic salt may include various types of phosphate, sulfate, and a metal salt of magnesium, potassium, manganese, iron, zinc, and the like.

Furthermore, vitamins such as biotin, pantothenic acid, inositol or nicotinic acid, or factors for promoting growth such as nucleoside or amino acid, may also be added, as necessary.

Still further, in order to reduce foaming occurring during the reaction, it is desired to add an appropriate amount of commercially available antifoaming agent into a culture solution.

As a reaction solution used in the present invention, water, a buffer solution, a medium or the like are used. Of these, a medium is most preferable. A medium comprises, for example, the above-described organic material, and a carbonate ion, bicarbonate ion, or carbon dioxide, and these components can be reacted under anaerobic conditions. A carbon ion or bicarbonate ion is supplied from carbonic acid, bicarbonic acid, a salt thereof, or carbon dioxide. Specific examples of salts of carbonic acid or bicarbonic acid may include ammonium carbonate, sodium carbonate, potassium carbonate, ammonium bicarbonate, sodium bicarbonate, and potassium bicarbonate. Such a carbonate ion or bicarbonate ion is added at a concentration between 1 mM and 500 mM, preferably between 2 mM and 300 mM, and more preferably between 3 mM and 200 mM. When carbon dioxide is added to a medium, it is added therein in an amount between 50 mg and 25 g, preferably between 100 mg and 15 g, and more preferably between 150 mg and 10 g per L of the solution.

The pH of a culture solution and a reaction solution is adjusted to generally between pH 5 and pH 10, and preferably between pH 6 and pH 9.5. Even during the reaction, the pH of the culture solution is adjusted in the above range, as necessary, by addition of an alkaline substance, carbonate, urea, etc.

The optimal temperature for the growth of microorganisms used in the reaction is generally between 25° C. and 35° C. The temperature during the reaction is generally between 25° C. and 40° C., and preferably between 30° C. and 37° C.

The reaction is carried out generally for 5 to 120 hours. The amount of cell used in the reaction is not particularly limited, but the cell is used in an amount of 1 to 700 g/L, preferably 10 to 500 g/L, and more preferably 20 to 400 g/L.

Aeration and stirring should be carried out during the culture, so as to supply oxygen. Such aeration and stirring may also be carried out during the reaction. However, even if aeration is not carried out and no oxygen is supplied during the reaction, it is not problematic. The term "anaerobic conditions" used herein means that the reaction is carried out under conditions where the concentration of dissolved oxygen in a solution is set at low. In this case, it is desired that the reaction is carried out at a concentration of dissolved oxygen between 0 and 2 ppm, preferably between 0 and 1 ppm, and more preferably between 0 and 0.5 ppm. As a method for adjusting the concentration of dissolved oxygen in the above range, a method of hermetically closing a container so as to perform the reaction without aeration, a method of supplying inactive gas such as nitrogen gas during the reaction, and a method of supplying inactive gas containing carbon dioxide, etc. can be applied.

In general, the synthesis reaction of organic acid is terminated when an organic material such as glucose contained in the culture solution is exhausted. At that time, organic acids such as succinic acid, malic acid or fumaric acid are generated in the reaction solution. Of these organic acids, succinic acid is accumulated at the highest level, and thus, it is preferable as a product.

In the present invention, an aqueous reaction solution is recovered after completion of the reaction. The term "after completion of the reaction" used herein means that the remaining organic material (for example, glucose) is 50% or less of the initial additive amount, preferably 20% or less thereof, and more preferably 5% or less thereof. Otherwise, the above term is also used to mean that the concentration of the remaining material is 5% by weight or less, preferably 2% by weight or less, and more preferably 0.5% by weight or less.

In the present invention, as stated above, after completion of the synthesis reaction of organic acid, an aqueous reaction solution is recovered, cell or treated products thereof are separated from the recovered aqueous reaction solution, and the thus separated cell or treated products thereof are allowed to act on a fresh aqueous reaction solution, so that the production of organic acid can be carried out again. Separation of the cell or treated products thereof from the recovered aqueous reaction solution can be carried out by methods known to a person skilled in the art, such as centrifugation.

In addition, using the total amount or a part of the recovered aqueous reaction solution, the cell or treated products thereof can be separated. It is preferred that the total amount of the recovered aqueous reaction solution is used. The separated cell or treated products thereof are allowed to act on a fresh aqueous reaction solution. The term "fresh aqueous reaction solution" used herein means an aqueous reaction solution containing an organic material such as glucose.

As stated above, when cell or treated products thereof are repeatedly used, the production amount of organic acid in the second process and the subsequent processes is preferably 80% or more, more preferably 90% or more, and particularly preferably 95% or more with respect to the production amount thereof in the first process. In a particularly preferred example, the production amount of succinic acid in the second process and the subsequent processes is 80% or more, more preferably 90% or more, and particularly preferably 95% or more with respect to the production amount thereof in the first process.

In the present invention, cell or treated products thereof can be repeatedly used twice or more. The number of reuse of the cell or treated products thereof is 3 or more times. The upper limit of the number of reuse is not particularly limited, as long as organic acid is produced. The cell or treated products thereof can be repeatedly used, for example, 10 times, 20 times, 30 times, or more desired times.

In the reaction solution obtained by the above-described method of the present invention, organic acids such as succinic acid, malic acid or fumaric acid are generated. This organic acid-containing composition is also included in the scope of the present invention. An organic acid-containing composition with a high level of accumulation of succinic acid is particularly preferable.

Organic acid accumulated in the reaction solution (culture solution) can be separated or purified from the reaction solution according to conventional methods. More specifically, solids such as cell are removed by centrifugation, filtration, or the like, and then, desalination is carried out with ion exchange resin or the like. Thereafter, organic acid can be separated or purified from the resultant solution by crystallization or column chromatography.

Moreover, in the present invention, organic acid is produced by the above-described method of the present invention, and then, a polymerization reaction is carried out using the obtained organic acid as a starting material, so that an organic acid-containing polymer can be produced.

In recent years, as the number of industrial products concerning for the environment has been increased, polymers which are produced from materials derived from plants have become a focus of attention. The organic acid which is produced in the present invention can be processed into a polymer such as polyester or polyamide for use. In addition, such organic acid can be directly used as a food additive, pharmaceutical or cosmetic, or it can be used as an intermediate thereof.

The present invention will be further specifically described in the following examples. However, the scope of the present invention is not limited to these examples.

EXAMPLE

Example 1

MJ233AB-41LDH(−) strain, which lacks lactate dehydrogenase (LDH), was prepared from *Brevibacterium flavum* MJ233AB-41 (FERM BP-1498) according to JP Patent Publication (Kokai) No. 11-206385 A (1999). This is to say, total DNA which was extracted from the MJ-233 strain by a conventional method was used as a template, a PCR reaction was carried out using two primers described in JP Patent Publication (Kokai) No. 11-206385 A (1999), which were CARAARCCNG GNGARAC (SEQ ID NO: 1) and TCNCCRTGYT CNCCNAT (SEQ ID NO: 2) (wherein R represents A or G, Y represents C or T, and N represents A, G, C, or T). 3 µl of the obtained reaction solution was mixed with 1 µl of a PCR product cloning vector pGEM-T (commercially available from PROMEGA). 50 mM Tris buffer solution (pH 7.6), 10 mM dithiothreitol, 1 mM ATP, 10 mM $MgCl_2$, and 1 unit of T4 DNA ligase were added to the obtained mixture. The mixture was then reacted at 4° C. for 15 hours to perform ligation. *Escherichia coli* JM109 (manufactured by Takara Shuzo Co., Ltd.) was transformed with the obtained plasmid mixed solution by the calcium chloride method. The transformant was then applied to a medium (which was produced by dissolving 10 g of tryptone, 5 g of a yeast extract, 5 g of NaCl, and 16 g of an agar in 1 L of distilled water) containing 50 mg of ampicillin.

Strains growing on this medium were subjected to a liquid culture according to a conventional method, and plasmid DNA was prepared from the culture solution. 50 mM Tris buffer solution (pH 7.5), 1 mM dithiothreitol, 10 mM $MgCl_2$, 100 mM NaCl, 1 unit each of restriction enzymes SphI and SalI were added to 20 µl of the plasmid DNA, and the mixture was reacted at 37° C. for 1 hour. 300-bp fragment was recovered from the obtained DNA solution, using Gene Clean II (manufactured by Funakoshi). 10 µl of the DNA solution, a cloning vector pHSG396 (manufactured by Takara Shuzo Co., Ltd.) that was resistant to chloramphenicol, and 1 µl of a SphI and SalI cleavage product were mixed. 50 mM Tris buffer solution (pH 7.6), 10 mM dithiothreitol, 1 mM ATP, 10 mM $MgCl_2$, and 1 unit of T4 DNA ligase were added to the mixture, followed by reaction at 4° C. for 15 hours to perform ligation. *Escherichia coli* JM109 (manufactured by Takara Shuzo Co., Ltd.) was transformed with the obtained plasmid mixed solution by the calcium chloride method. The transformant was then applied to a medium (which was produced by dissolving 10 g of tryptone, 5 g of a yeast extract, 5 g of NaCl, and 16 g of an agar in 1 L of distilled water) containing 50 mg of ampicillin.

Strains growing on this medium were subjected to a liquid culture according to a conventional method, and plasmid DNA was prepared from the culture solution. The plasmid was introduced into *Brevibacterium flavum* MJ-233 by the electric pulse method. The obtained transformant was applied to a medium (which was produced by dissolving 2 g of urea, 7 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate hydrate, 200 µg of D-biotin, 200 µg of thiamine hydrochloride, 1 g of a yeast extract, 1 g of casamino acid, and 16 g of agar in 1 L of distilled water) containing 5 mg of chloramphenicol. From among strains growing on this medium, strains whose LDH activity became one-tenth or less of the normal level were selected. This strain was named as MJ233AB-41LDH(−).

100 ml of a medium of 4 g of urea, 14 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate hydrate, 200 µg of D-biotin, 200 µg of thiamine hydrochloride, 1 g of a yeast extract, 1 g of casamino acid, and 1,000 ml of distilled water, was placed in a 500-ml Erlenmeyer flask, followed by sterilization by heating at 120° C. for 20 minutes. Thereafter, the medium was cooled to room temperature. 4 ml of a 50% glucose aqueous solution that had previously been sterilized and 5 ml of a 0.1% chloramphenicol aqueous solution that had been aseptically filtrated, were added thereto. The aforementioned MJ233AB-41LDH(−) strain was then inoculated into the medium, and a seed culturing was then carried out at 30° C. for 24 hours.

A medium of 1.6 g of urea, 5.6 g of ammonium sulfate, 0.2 g of monopotassium phosphate, 0.2 g of dipotassium phosphate, 0.2 g of magnesium sulfate heptahydrate, 8 mg of ferrous sulfate heptahydrate, 8 mg of manganese sulfate hydrate, 80 µg of D-biotin, 80 µg of thiamine hydrochloride, 0.4 g of a yeast extract, 0.4 g of casamino acid, 0.4 ml of an antifoaming agent (Adekanol LG-294; manufactured by Asahi Denka Co., Ltd.), and 200 ml of distilled water was placed in a 1 L fermenter, followed by sterilization by heating at 120° C. for 20 minutes. Thereafter, the medium was cooled to room temperature. Then, 200 ml of a 20% glucose aqueous solution that had previously been sterilized was added thereto. The total amount of the aforementioned seed culture solution was added to the medium, and the temperature was kept at 30° C. The pH of the medium was adjusted to 8.0 by means of 2 M sodium carbonate. The reaction was carried out under aeration of 100 ml/minute (wherein the concentration of dissolved oxygen in the reaction solution was kept at 2 ppm or lower during the reaction), while stirring at 400 rotations/minute. 31 hours later, glucose was almost exhausted, and succinic acid was accumulated at a level of 31 g/L.

Example 2

All amount of the culture solution obtained in Example 1 was centrifuged at 10,000 rpm for 10 minutes, so as to collect cells. The same medium as used in Example 1 was added thereto, and the mixture was kept at 30° C. The pH of the mixture was adjusted to 8.0 by means of 2 M sodium carbonate. The reaction was carried out under aeration of 100 ml/minute (wherein the concentration of dissolved oxygen in the reaction solution was kept at 2 ppm or lower during the reaction), while stirring at 400 rotations/minute. 21 hours later, glucose was almost exhausted, and 42 g/L of succinic acid, 2.2 g/L of fumaric acid, 3.7 g/L of acetic acid, 0.8 g/L of malic acid, 1.9 g/L of pyruvic acid, and 0.1 g/L of oxaloacetic acid were accumulated respectively.

Example 3

All amount of the culture solution obtained in Example 2 was centrifuged at 10,000 rpm for 10 minutes, so as to collect cells. The same medium as used in Example 1 was added thereto, and the mixture was kept at 30° C. The pH of the mixture was adjusted to 8.0 by means of 2 M sodium carbonate. The reaction was carried out under aeration of 100 ml/minute (wherein the concentration of dissolved oxygen in the reaction solution was kept at 2 ppm or lower during the reaction), while stirring at 400 rotations/minute. 20 hours later, glucose was almost exhausted, and 47 g/L of succinic acid, 1.3 g/L of fumaric acid, 12 g/L of acetic acid, 0.6 g/L of malic acid, 2.0 g/L of pyruvic acid, and 0.1 g/L of oxaloacetic acid were accumulated.

Examples 4 to 11

The reaction was carried out under the same conditions as in Example 3. 22 hours later, the reaction was terminated, and the cells were repeatedly used. The production amounts of various types of organic acids are shown in the following Table 1.

TABLE 1

| Examples | Glucose (g/L) | Succinic acid (g/L) | Fumaric acid (g/L) | Acetic acid (g/L) | Malic acid (g/L) | Pyruvic acid (g/L) | Oxaloacetic acid (g/L) |
|---|---|---|---|---|---|---|---|
| 4 | 0.0 | 50.0 | 0.8 | 11.8 | 0.9 | 2.5 | 0.2 |
| 5 | 0.0 | 50.0 | 0.8 | 12.1 | 0.9 | 1.9 | 0.1 |
| 6 | 0.0 | 47.0 | 0.8 | 11.4 | 1.0 | 2.4 | 0.2 |
| 7 | 0.0 | 45.3 | 0.7 | 10.3 | 1.0 | 2.8 | 0.3 |
| 8 | 0.0 | 48.0 | 0.8 | 8.2 | 1.7 | 5.2 | 0.3 |
| 9 | 0.0 | 49.3 | 0.9 | 9.1 | 1.4 | 6.8 | 0.2 |
| 10 | 0.0 | 45.9 | 1.0 | 9.0 | 1.2 | 4.3 | 0.2 |
| 11 | 0.0 | 47.9 | 0.8 | 7.8 | 1.2 | 7.6 | 0.2 |

INDUSTRIAL APPLICABILITY

According to the method of the present invention, organic acid of interest can be obtained at a high reaction rate and with a high yield in the production of organic acid using bacteria.

The present application claims priority based on Japanese Patent Application (Patent Application No. 2003-194240) filed on Jul. 9, 2003; the disclosure of which is incorporated herein by reference. In addition, all publications cited herein are also incorporated herein by reference in their entirety.

The invention claimed is:

1. A method for producing at least one organic acid selected from the group consisting of succinic acid, malic acid, and fumaric acid by a bacterial cell which lacks lactate dehydrogenase (LDH) and is selected from the group consisting of Coryneform bacteria, Bacillus bacteria, Rhizobium bacteria, Brevibacterium bacteria, and Arthrobacter bacteria, the method comprising:
   a first process of allowing the bacterial cell to act on a reaction solution comprising water, a buffer solution, or a medium and at least one fermentable sugar, to produce said organic acid, and after completion of the reaction separating the bacterial cell from the reaction solution; and
   a second process of allowing the separated bacterial cell to act on a fresh reaction solution comprising at least one fermentable sugar.

2. The method according to claim 1, wherein the bacterial cell is any one selected from the group consisting of Coryneform bacteria, Bacillus bacteria, and Rhizobium bacteria.

3. The method according to claim 1 wherein the bacterial cell is a mutant bacterial cell, whose ability to produce lactic acid is reduced to 10% or less when compared with that of wild-type bacteria.

4. The method according to claim 1, wherein the reaction solution contains carbonate ion, bicarbonate ion, or carbon dioxide.

5. The method according to claim 1, wherein the bacterial cell is allowed to act on the reaction solution under an anaerobic atmosphere.

6. The method according to claim 1, wherein the fermentable sugar is glucose.

7. The method according to claim 1, comprising repeating the second process 3 or more times.

8. The method according to claim 1, wherein after completion of the reaction, a total amount of the reaction solution is used as it is in a subsequent process.

9. The method according to claim 7, wherein the amount of organic acid produced in the second process and subsequent processes is 80% or more with respect to the production amount thereof in the first process.

10. The method according to claim 9, wherein the organic acid produced comprises succinic acid.

11. An organic acid-containing composition which is produced by the method of claim 1, wherein the organic acid-containing composition further comprises a salt of carbonic acid or a salt of bicarbonic acid.

12. The organic acid-containing composition according to claim 11, wherein the organic acid is succinic acid.

13. The method according to claim 1, wherein the bacterial cell is an immobilized cell.

* * * * *